(12) United States Patent
Clower et al.

(10) Patent No.: US 10,016,454 B2
(45) Date of Patent: Jul. 10, 2018

(54) SILANE-CONTAINING MOISTURE-CURABLE TISSUE SEALANT

(71) Applicant: Cohera Medical, Inc., Pittsburgh, PA (US)

(72) Inventors: Dottie Clower, Pittsburgh, PA (US); Despina Dobbins, Gibsonia, PA (US); Stephanie Kladakis, Pittsburgh, PA (US)

(73) Assignee: Cohera Medical, Inc., Raleigh, NC (US)

( * ) Notice: Subject to any disclaimer, the term of this patent is extended or adjusted under 35 U.S.C. 154(b) by 605 days.

(21) Appl. No.: 13/693,218

(22) Filed: Dec. 4, 2012

(65) Prior Publication Data

US 2014/0154204 A1   Jun. 5, 2014

(51) Int. Cl.
*A61K 31/765* (2006.01)
*A61K 31/80* (2006.01)

(52) U.S. Cl.
CPC ...... *A61K 31/80* (2013.01); *F04C 2270/0421* (2013.01)

(58) Field of Classification Search
None
See application file for complete search history.

(56) References Cited

U.S. PATENT DOCUMENTS

| | | | |
|---|---|---|---|
| 3,941,733 A * | 3/1976 | Chang | C08G 18/0804 428/304.4 |
| 4,376,149 A | 3/1983 | Martin | |
| 5,990,257 A | 11/1999 | Johnston et al. | |
| 6,046,270 A | 4/2000 | Roesler et al. | |
| 6,046,295 A | 4/2000 | Frisch, Jr. et al. | |
| 6,077,902 A | 6/2000 | Roesler et al. | |
| 6,096,823 A | 8/2000 | Shaffer | |
| 6,162,241 A | 12/2000 | Coury et al. | |
| 6,310,170 B1 | 10/2001 | Johnston et al. | |
| 6,458,889 B1 | 10/2002 | Trollsas et al. | |
| 6,809,170 B2 | 10/2004 | Roesler et al. | |
| 6,833,423 B2 | 12/2004 | Roesler et al. | |
| 6,844,413 B2 | 1/2005 | Roesler et al. | |
| 6,887,964 B2 | 5/2005 | Frisch et al. | |
| 6,998,459 B2 | 2/2006 | Roesler et al. | |
| 7,091,298 B2 | 8/2006 | Schindler et al. | |
| 7,115,696 B2 | 10/2006 | Roesler et al. | |
| 7,153,923 B2 | 12/2006 | Schindler et al. | |
| 7,319,128 B2 | 1/2008 | Ziche et al. | |
| 7,332,541 B2 | 2/2008 | Schindler et al. | |
| 7,858,078 B2 | 12/2010 | Hadba et al. | |
| 7,998,466 B2 | 8/2011 | Hadba et al. | |
| 8,044,234 B2 | 10/2011 | Hadba et al. | |
| 8,133,964 B2 | 3/2012 | Iezzi | |
| 2004/0224168 A1 | 11/2004 | Jennings et al. | |
| 2004/0225077 A1 * | 11/2004 | Gravett et al. | 525/418 |
| 2006/0199933 A1 | 9/2006 | Okamoto et al. | |
| 2007/0167598 A1 | 7/2007 | Stanjek et al. | |
| 2008/0057317 A1 | 3/2008 | Kettner et al. | |
| 2008/0312369 A1 | 12/2008 | Beers et al. | |
| 2009/0030145 A1 | 1/2009 | Johnston et al. | |
| 2009/0124751 A1 | 5/2009 | Lucas et al. | |
| 2009/0214879 A1 | 8/2009 | Jucker et al. | |
| 2010/0043945 A1 | 2/2010 | Dohner et al. | |
| 2011/0301639 A1 | 12/2011 | Beckman | |

FOREIGN PATENT DOCUMENTS

WO   WO 2011150199 A2 * 12/2011
WO   WO 2011163180 A1 * 12/2011   ......... C08G 18/10

OTHER PUBLICATIONS

International Search Report and Written Opinion in International Application No. PCT/US2013/072757, dated Apr. 25, 2014, 13 pages.

* cited by examiner

*Primary Examiner* — James W Rogers
(74) *Attorney, Agent, or Firm* — Fish & Richardson P.C.

(57) ABSTRACT

A tissue sealant that includes the reaction product of (a) a polyol; (b) a polyisocyanate; and (c) an alkoxy silane having the formula: $(R^1R^2R^3)$—Si—$CH_2$—Z where (i) Z is an —OH, —SH, —NCO, or —$NHR^4$ group, where $R^4$ is hydrogen, an alkyl group, or an aryl group; and (ii) each $R^1$, $R^2$, and $R^3$, independently, is H, an alkoxy group, an alkyl group, a heteroalkyl group other than an alkoxy group, an aryl group, or a heteroaryl group, with the proviso that at least two of $R^1$, $R^2$, and $R^3$ are alkoxy groups, the relative amounts of the polyol, polyisocyanate, and alkoxy silane being selected such that the reaction product comprises free isocyanate groups. The tissue sealant is moisture-curable and biodegradable in a physiological environment.

19 Claims, No Drawings

SILANE-CONTAINING MOISTURE-CURABLE TISSUE SEALANT

TECHNICAL FIELD

This invention relates to moisture-curable sealants for sealing biological tissue.

BACKGROUND

Tissue sealants are typically used to stop bleeding during vascular or liver surgery, eliminate air leaks in the lungs, and to prevent adhesions. Examples of sealants used for this purpose include fibrin products, polyethylene glycol products, and albumin-based products. In each case, the tissue sealant consists of two distinct components that are mixed together just prior to application to tissue to cause a rapid, irreversible chemical reaction. This reaction transforms the mixture from a low viscosity liquid into an elastic solid that coats the target tissue. The sealants are designed to degrade within a set period of time that typically ranges from days to weeks. One problem with such two-part sealants, however, is that the rapid cure times can cause the sealant applicator to clog.

SUMMARY

A tissue sealant is described that includes the reaction product of (a) a polyol; (b) a polyisocyanate; and (c) an alkoxy silane. The alkoxy silane has the formula: $(R^1R^2R^3)$—Si—$CH_2$—Z where (i) Z is an —OH, —SH, —NCO, or —$NHR^4$ group, where $R^4$ is hydrogen, an alkyl group, or an aryl group; and (ii) each $R^1$, $R^2$, and $R^3$, independently, is H, an alkoxy group, an alkyl group, a heteroalkyl group other than an alkoxy group, an aryl group, or a heteroaryl group, with the proviso that at least two of $R^1$, $R^2$, and $R^3$ are alkoxy groups. The relative amounts of the polyol, polyisocyanate, and alkoxy silane are selected such that the reaction product includes free isocyanate groups. The tissue sealant is moisture-curable and biodegradable in a physiological environment.

As used herein, the term "alkyl" includes straight chain, branched, and cyclic alkyl groups.

In some embodiments, the tissue sealant also includes an isocyanate-functional organosilane. The isocyanate-functional organosilane has at least one free isocyanate group and at least one terminal silane group having the formula: $(R^5R^6R^7)$—Si— where each $R^5$, $R^6$, and $R^7$, independently, is H, an alkoxy group, an alkyl group, a heteroalkyl group other than an alkoxy group, an aryl group, or a heteroaryl group.

In some embodiments, two of $R^1$, $R^2$, and $R^3$ are $C_1$-$C_6$ alkoxy groups. In other embodiments, each of $R^1$, $R^2$, and $R^3$ is a $C_1$-$C_6$ alkoxy group. Examples of suitable Z groups include an —$NHR^4$ group, e.g., where $R^4$ is a phenyl group.

In some embodiments, the isocyanate-functional organosilane has a molecular weight no greater than 500 g/mole, while in other embodiments it has a molecular weight no greater than 300 g/mole.

In some embodiments, at least one of $R^5$, $R^6$, and $R^7$ of the isocyanate-functional organosilane is a $C_1$-$C_6$ alkoxy group. In other embodiments, each of $R^5$, $R^6$, and $R^7$ of the isocyanate-functional organosilane is a $C_1$-$C_6$ alkoxy group.

One example of a suitable isocyanate-functional organosilane is a compound having the formula: $(R^5R^6R^7)$—Si—$R^8$—NCO where $R^8$ is a $C_1$-$C_{10}$ alkyl group. Another example has the formula: $(R^5R^6R^7)$—Si—$R^8$—NCO where each of $R^5$, $R^6$, and $R^7$ is a $C_1$-$C_6$ alkoxy group, and $R^8$ has the formula: —$(CH_2)_n$— where n=1-10.

The polyol may be selected from the group consisting of polyether polyols, polyester polyols, co-polyester polyether polyols, alkoxylated glycerol derivatives, and combinations thereof. The polyisocyanate may be selected from the group consisting of lysine diisocyanate and derivatives thereof, lysine triisocyanate and derivatives thereof, and combinations thereof.

In some embodiments, the tissue sealant includes the reaction product of the alkoxy silane, the polyisocyanate, and at least two different polyols. Two polyols are "different" from each other if they have different molecular weights and/or chemical structures.

The tissue sealant can also include at least one reagent selected from the group consisting of solvents, diluents, coagulents, catalysts, and combinations thereof. The tissue sealant can also include a colorant such as beta-carotene.

In use, the sealant is applied to a tissue surface, and cured in the presence of moisture associated with the tissue to seal the tissue surface. Because the sealant is a one-component composition (i.e. it includes one active molecule that moisture cures upon application to tissue), it is not necessary to mix two components prior to tissue application, thereby simplifying application from the user's perspective and avoiding the applicator clogging problems associated with two-component tissue sealants.

The sealant is stable in the absence of moisture, thus facilitating storage. The sealant also adheres well to biological tissue, particularly when the isocyanate-functional organosilane is included, and has good mechanical properties.

The details of one or more embodiments of the invention are set forth in the description below. Other features, objects, and advantages of the invention will be apparent from the description and from the claims.

DETAILED DESCRIPTION

The tissue sealant includes the reaction product of a polyol, a polyisocyanate, and an alkoxy silane. The stoichiometry of the reactants is selected such that the resulting reaction product has free (i.e. unreacted) isocyanate groups.

The alkoxy silane has the formula: $(R^1R^2R^3)$—Si—$CH_2$—Z where (i) Z is an —OH, —SH, —NCO, or —$NHR^4$ group. $R^4$ is a hydrogen, an alkyl group (e.g., a $C_1$-$C_6$ alkyl group), or an aryl group (e.g., having at least one ring such as a phenyl group). Each $R^1$, $R^2$, and $R^3$, independently, is H, an alkoxy group (e.g., a $C_1$-$C_6$ alkoxy group), an alkyl group (e.g., a $C_1$-$C_6$ alkyl group), a heteroalkyl group other than an alkoxy group (e.g., an alkyl amido or amido group), an aryl group (e.g., a phenyl group), or a heteroaryl group (e.g., a pyrrolyl, furyl, or pyridinyl group), with the proviso that at least two of $R^1$, $R^2$, and $R^3$ are alkoxy groups. The alkyl groups may be straight chain, branched, or cyclic alkyl groups.

The polyol includes at least two hydroxyl groups available for reaction. Examples of suitable polyols include polyether polyols, polyester polyols, co-polyester polyols, and alkoxylated glycerol derivatives (e.g., glycerol ethoxylate). Specific examples of polyether polyols include polyethylene and polypropylene glycols. Specific examples of polyester polyols include polycaprolactone and polylactide diols. Typical polyols have molecular weights less than 10,000. In some embodiments, the polyol may have a molecular less than 5,000 or less than 2,000. Mixtures of two or more different polyols can be used as well. For example, diols and triols can be used in combination with each other.

The polyisocyanate includes at least two isocyanate groups available for reaction. The polyisocyanate may be selected from the group consisting of lysine diisocyanate and derivatives thereof, lysine triisocyanate and derivatives thereof, and combinations thereof.

The sealant may also include an isocyanate-functional organosilane. The isocyanate-functional organosilane has at least one free isocyanate group and at least one terminal silane group having the formula: $(R^5R^6R^7)$—Si— where each $R^5$, $R^6$, and $R^7$, independently, is H, an alkoxy group (e.g., a $C_1$-$C_6$ alkoxy group), an alkyl group (e.g., a $C_1$-$C_6$ alkyl group), a heteroalkyl group other than an alkoxy group (e.g., an alkyl amido or amido group), an aryl group (e.g., a phenyl group), or a heteroaryl group (e.g., a pyrrolyl, furyl, or pyridinyl group).

In general, the isocyanate-functional organosilane is included in an amount of up to 15% by weight, based upon the weight of the composition. In some embodiments, it is included in an amount of up to 8% by weight, while in other embodiments the amount is up to 3% by weight.

The sealants may further contain one or more reagents selected from the group consisting of solvents, diluents, coagulents, catalysts, and combinations thereof. The reagents preferably are inert towards the polyol, polyisocyanate, alkoxy silane, and isocyanate-functional organosilane, and thus do not interfere with the reaction among these compounds.

Examples of suitable catalysts include tertiary amines (e.g., aliphatic tertiary amines), organometallic compounds (e.g., bismuth salts and zirconium chelates), Bronsted acids, and protonic acids (e.g., sulfuric or hydrochloric acid). Examples of useful coagulents include calcium salts.

The solvents and diluents may be used to modify the rheology of the sealant. Examples of suitable solvents include dimethylsulfoxide (DMSO), dimethylformamide (DMF), tetrahydrofuran (THF), glyme, and combinations thereof. Examples of suitable non-volatile diluents include dimethylsulfoxide (DMSO), propylene carbonate, diglyme, polyethylene glycol diacetates, polyethylene glycol dicarbonates, dimethylisosorbide, ethyl pyruvate, triacetin, triethylene glycol, and combinations thereof. Examples of suitable volatile diluents include hydrocarbons, perfluoroalkanes, hydrofluoroalkanes, carbon dioxide, and combinations thereof. A single reagent can perform multiple roles. Thus, for example, DMSO can function as both a solvent and a non-volatile diluent. The sealants may also include one or more stabilizers. Examples include antioxidants (e.g., BHT and BHA), water scavengers (e.g., acyl and aryl halides, and anhydrides), Bronsted acids, and the like. Bronsted acids may also be used as catalysts.

The sealant may also include a colorant to help a surgeon visualize the sealant during application to biological tissue. An example of a suitable colorant is beta-carotene.

The sealants are typically prepared by reacting the polyol, polyisocyanate, and alkoxy silane together, either in a single step reaction, in which reactants are combined together in a "single pot" reaction, or a multi-step reaction, in which the reactants are reacted sequentially. The resulting reaction product is then combined with the isocyanate-functional organosilane and any of the aforementioned ingredients.

EXAMPLES

Bonding Test

Porcine small intestine was acquired from Tissue Source (Indiana) and stored at −10° C. prior to use.

The intestine is washed thoroughly with cold water prior to testing. Sections of approximately 24 cm are prepared for use in bond testing; the sections are stored at 37° C. and 100% relative humidity prior to application of the sealant. Then at ambient conditions, the intestine sample is marked off in 3 sections (thirds) marked as "dry", "damp", and "wet"; the entire sample is then blotted dry. A sponge is soaked in phosphate buffered saline (PBS) and then squeezed over the "damp" and "wet" sections of the sample—subsequently the "damp" section is lightly blotted with a towel. At this point, sealant is applied to each of the sample sections via syringe—approximately 0.1 cc is used per application. The sealant is then allowed to cure for 20 minutes at room temperature and ambient relative humidity prior to testing. Each of the sealant strips is manipulated with a gloved finger—scoring is shown in the table below; data are reported as averages of 3 runs.

TABLE 1

Scoring of Bonding Test Results

| Bonding Score | Description |
|---|---|
| 0 | The sealant is easily removed with little to no manipulation or not fully cured |
| 1 | The sealant is slightly adhered, peels off the surface with manipulation in one piece |
| 2 | The sealant is slightly well adhered, requires some removal in pieces but then peels off in other places |
| 3 | The sealant is well adhered, requires removal in pieces |
| 4 | The sealant is strongly adhered, requires rigorous manual peeling for removal in pieces |
| 5 | The sealant is not removable, even with aggressive manipulation |

Burst Test

The test is conducted following ASTM F 2392-04, *Standard Test Method for Burst Strength of Surgical Sealants*.

Tack-Free Time

Porcine skin is acquired from Stellen Medical (Minnesota) and stored at −10° C. prior to use. The skin is cut into 3½ cm×3½ cm squares and stored at 37° C. and 100% relative humidity prior to application of the sealant.

Testing is then performed in a humidity controlled chamber at a target dew point of 0° C. An electronic pipette is used to apply 180ℓ of sealant to the skin within a 1.6 cm diameter application area. A timer is immediately initiated and the tack of the sample is checked with a stainless steel spatula every 30 seconds. Two minutes after sealant application, 1.0 cc of PBS is washed over the sealant. The state of tack is continually assessed in 30 second intervals until a total of 5 minutes have elapsed from the initial application.

TABLE 2

Tack Descriptions.

| Tack State | Description |
|---|---|
| Liquid | An uncured state |
| Stringy | A liquid state, when touched jelly like strands will pull away from the product |
| Partial Cure | A state that has formed a sticky cured top layer over an uncured bottom layer |

TABLE 2-continued

Tack Descriptions.

| Tack State | Description |
|---|---|
| Sticky/Tacky | A soft or solid cure that will stick to a gloved finger but retain its shape |
| Soft | A soft cured product with no tack |
| Solid | A firm/hard cured product with no tack |

Materials:

Polyethylene glycol (average molecular weight=1500) and polyethoxylated glycerol (average molecular weight=1000) were received from Aldrich Chemical Co. Ethyl pyruvate (97.5%), phenylaminomethyl triethoxysilane (97%), dimethyl sulfoxide (99.9%) and lysine (ethyl ester) di-isocyanate (LDI, 99.2%), and N-phenylaminomethyl triethoxysilane (99%) were received from Sigma-Aldrich Fine Chemicals and used as received. Sulfuric acid (99.999%), isocyanatopropyl triethoxysilane (95%), and methyl acetate (99.5%) were purchased from Aldrich Chemical Co and used as received.

Example 1: Synthesis of Sealants, First Step 40.5 g polyethylene glycol (M=1500, 54 mmol OH groups) and 22.9 g polyethoxylated glycerol (M=1000, 68.4 mmol OH groups) were added to a 250 cc 3-neck flask equipped with a mechanical stirrer. The temperature was raised to 120-140° C. and vacuum was applied for at least 15 hours to remove water. The temperature was raised to 80° C. and LDI (30.9 g, 273.8 mmol NCO) and sulfuric acid (0.0243 g) were added under nitrogen with stirring. The reaction was continued for 5-5½ hours until titration showed that 50% of the isocyanate groups had been consumed.

Example 2: Synthesis of Sealant with No Residual Isocyanate Groups and No Isocyanate-Functional Silane for Comparative Purposes Following the LDI-polymer reaction in Example 1, phenylaminomethyl triethoxysilane (40.7 g, 151.4 mmol amine) was added under nitrogen while maintaining temperature at 80° C. The reaction was allowed to continue until infra-red spectroscopy (at a wavelength of 2265 cm$^{-1}$) showed that all of the isocyanate groups had been consumed. At this point, 43.6 g ethyl pyruvate was added with stirring, followed by 0.01 g sulfuric acid. The resulting sealant was initially stored at 4° C.

| Lot | Tack Free Time | Bonding (Wet/Damp/Dry) | Burst Strength (mmHg) |
|---|---|---|---|
| 095-112 | Tack free @ 30 seconds | 3.3, 2.7, 2.7 | 28.9 |

Example 3. Synthesis of Sealant with Free Isocyanate Groups

Following the LDI-polymer reaction in Example 1, phenylaminomethyl triethoxysilane was added in a less-than-stoichiometric amount relative to the isocyanate groups present; for example 17.5 g (65.1 mmol). This addition was done under nitrogen while maintaining temperature at 80° C. The reaction was allowed to continue until infrared spectroscopy showed that the isocyanate concentration (2265 cm$^{-1}$) was not changing substantially over time. Ethyl pyruvate and sulfuric acid were added as in Example 2. Titration against dibutyl amine and acid demonstrated the presence of residual isocyanate groups in the material.

TABLE 3

Sealant with Various Amounts of Free Isocyanate

| Example # | % Silyl | % NCO | Tack Free Time | Bonding (Wet/Damp/Dry) | Burst Strength (mmHg) |
|---|---|---|---|---|---|
| 3a | 25 | 75 | Did not crosslink to a solid state/not testable | | |
| 3b | 40 | 60 | Tacky @ 5 min | 1, 1, 1 | 7.7 |
| 3c | 50 | 50 | 3.0 min | 4, 3, 3.7 | 115.6 |
| 3d | 60 | 40 | 0.5 min | 3, 3.3, 3 | 121.1 |
| 3e | 75 | 25 | NA | 3.3, 3.3, 3.3 | 48.3 |

The data in Table 3 show that the presence of free isocyanate groups improves the sealant performance versus that in Example 2 provided that the appropriate level of isocyanate groups is chosen.

Example 4. Synthesis of Sealants with Free Isocyanate Groups Plus Isocyanate-Functional Silane A sealant was synthesized as in examples 3. Following addition of the ethyl pyruvate, isocyanatopropyl triethoxysilane was added in amounts ranging from 4.8 g (19.4 mmol NCO) to 11.4 g (46.2 mmol NCO).

TABLE 4

Sealant with Free Isocyanate and Various Amount of Isocyanate-Functional Silane

| Example # | % Silyl | % NCO | % Isocyanate-Functional Silane | Tack Free Time | Bonding (Wet/Damp/Dry) | Burst Strength (mmHg) |
|---|---|---|---|---|---|---|
| 4a | 55 | 45 | 3.0% | 2.0 min | 4, 4, 4 | 195.5 |
| 4b | 55 | 45 | 5.6% | 0.5 min | 4, 4, 3 | 172.2 |
| 4c | 55 | 45 | 7.1% | 1.0 min | 4, 4, 4 | 172.5 |

In comparing the results in Tables 3 and 4, it can be seen that the addition of the isocyanatopropyl triethoxysilane improves both bonding and burst strength versus the sealants with residual isocyanate groups only at the chain ends of the prepolymer.

A number of embodiments of the invention have been described. Nevertheless, it will be understood that various modifications may be made without departing from the spirit and scope of the invention. Accordingly, other embodiments are within the scope of the following claims.

What is claimed is:

1. A tissue sealant comprising the reaction product of:
    (a) a polyol;
    (b) a polyisocyanate selected from the group consisting of lysine diisocyanate and derivatives thereof, lysine triisocyanate and derivatives thereof, and combinations thereof; and
    (c) an alkoxy silane having the formula: $(R^1R^2R^3)$—Si—$CH_2$—Z where:

(i) Z is an —OH, —SH, —NCO, or —NHR$^4$ group, where R$^4$ is hydrogen, an alkyl group, or an aryl group; and (ii) each R$^1$, R$^2$, and R$^3$, independently, is H, an alkoxy group, an alkyl group, a heteroalkyl group other than an alkoxy group, an aryl group, or a heteroaryl group, with the proviso that at least two of R$^1$, R$^2$, and R$^3$ are alkoxy groups, wherein the relative amounts of the polyol, polyisocyanate, and alkoxy silane are selected such that the number of isocyanate groups available for reaction is greater than the number of isocyanate-reactive groups available for reaction selected from the group consisting of —OH groups, —SH groups, —NHR$^4$ groups, and combinations thereof, and produces a reaction product that comprises free isocyanate groups, wherein the tissue sealant is moisture-curable and biodegradable in a physiological environment.

2. A tissue sealant according to claim 1 further comprising an isocyanate-functional organosilane having at least one free isocyanate group and at least one terminal silane group having the formula: (R$^5$R$^6$R$^7$)—Si— where each R$^5$, R$^6$, and R$^7$, independently, is H, an alkoxy group, an alkyl group, a heteroalkyl group other than an alkoxy group, an aryl group, or a heteroaryl group.

3. A tissue sealant according to claim 2 wherein the isocyanate-functional organosilane has a molecular weight no greater than 500 g/mole.

4. A tissue sealant according to claim 2 wherein the isocyanate-functional organosilane has a molecular weight no greater than 300 g/mole.

5. A tissue sealant according to claim 2 wherein the isocyanate-functional organosilane has the formula: (R$^5$R$^6$R$^7$)—Si—R$^8$—NCO where R$^8$ is a C$_1$-C$_{10}$ alkyl group.

6. A tissue sealant according to claim 1 wherein two of R$^1$, R$^2$, and R$^3$ are C$_1$-C$_6$ alkoxy groups.

7. A tissue sealant according to claim 1 wherein each of R$^1$, R$^2$, and R$^3$ is a C$_1$-C$_6$ alkoxy group.

8. A tissue sealant according to claim 1 wherein Z is an —NHR$^4$ group.

9. A tissue sealant according to claim 8 where R$^4$ is a phenyl group.

10. A tissue sealant according to claim 2 wherein at least one of R$^5$, R$^6$, and R$^7$ is a C$_1$-C$_6$ alkoxy group.

11. A tissue sealant according to claim 2 wherein each of R$^5$, R$^6$, and R$^7$ is a C$_1$-C$_6$ alkoxy group.

12. A tissue sealant according to claim 2 wherein each of R$^5$, R$^6$, and R$^7$ is a C$_1$-C$_6$ alkoxy group, and the isocyanate-functional organosilane has the formula: (R$^5$R$^6$R$^7$)—Si—R$^8$—NCO where R$^8$ has the formula: —(CH$_2$)$_n$— where n=1-10.

13. A tissue sealant according to claim 1 wherein the polyol is selected from the group consisting of polyether polyols, polyester polyols, co-polyester polyether polyols, alkoxylated glycerol derivatives, and combinations thereof.

14. A tissue sealant according to claim 1 wherein the tissue sealant comprises the reaction product of the alkoxy silane, the polyisocyanate, and at least two different polyols.

15. A tissue sealant according to claim 1, wherein the tissue sealant further comprises at least one reagent selected from the group consisting of solvents, diluents, catalysts, coagulants, and combinations thereof.

16. A tissue sealant according to claim 1, wherein the tissue sealant further comprises a colorant.

17. A tissue sealant according to claim 16, wherein the colorant comprises beta-carotene.

18. A method of sealing tissue comprising:
(a) applying a sealant according to claim 1 to a tissue surface; and
(b) curing the sealant to seal the area of tissue to which the sealant was applied.

19. A tissue sealant according to claim 1, wherein the tissue sealant further comprises ethyl pyruvate.

* * * * *